United States Patent [19]

Hardy et al.

[11] Patent Number: 5,702,692
[45] Date of Patent: Dec. 30, 1997

[54] HAIR COMPOSITION

[75] Inventors: Eugene E. Hardy, Freehold; Anthony Psihoules, Somerville, both of N.J.

[73] Assignee: Colgate-Palmolive Company, New York, N.Y.

[21] Appl. No.: 808,766

[22] Filed: Mar. 3, 1997

[51] Int. Cl.$^6$ .................................................. A61K 6/00
[52] U.S. Cl. ........................ 424/70.1; 424/401; 514/880
[58] Field of Search .................. 514/880; 424/70.1, 424/401

[56] References Cited

PUBLICATIONS

BASF, Luvimer 100P Provisional Technical Information, Apr. 1994, 1–16.
BASF, Luviskol VA 37 HM Provisional Technical Information, Sep. 1995, 1–12.
BASF, Material Safety Data Sheet Luviskol VA 37 HM, Apr. 2, 1996, 1–5.
BASF, Material Safety Data Sheet, Luvimer 100P, Oct. 23, 1995 1–5.
BASF Cosmeticon Luviskol VA 37 HM, 1–4 (1997).
BASF, Cosmeticon Luvimer 100P Resin, 1–4 (1997).

*Primary Examiner*—Terressa Mosley
*Attorney, Agent, or Firm*—Martin B. Barancik

[57] ABSTRACT

A sprayable hair fixing composition having the following components or reaction products comprising a) from about 0.5 to about 10 wt. % of a high molecule weight copolymer of polyvinylpyrrolidine and vinylacetate, the weight average molecular weight of said polymer being at least about 200,000, b) from about 0.5 to about 8 wt. % of at least about 80 wt. % neutralized copolymer of tertiary butylacrylate, ethyl acrylate and methacrylic acid, and c) a solvent system compatible with the combination of copolymer a and copolymer b, the wt. % of a and b in the range of about 1:4 to about 4:1.

15 Claims, No Drawings

HAIR COMPOSITION

BACKGROUND OF THE INVENTION

Hair fixing compositions usually comprise solutions or suspensions with film forming natural or synthetic polymers. Numerous polymers have been used in hair fixing formulations such as natural materials as gums, shellacs, chitosan, and protein derivatives or synthetic polymers with specific applications in hair fixing technology such as polyvinylpyrrolidones, copolymers of polyvinylpyrrolidone vinyl acetate, acrylates, acrylate acrylamides, crotonic acid containing copolymers usually substantially neutralized with a basic component. Examples of such crotonic acid polymers include neutralized crotonic acid/vinylacetate, and crotonic acid/vinylacetate, vinylpropionate and the like. Combinations of various polymers are now known as the active components in hair fixative formulations such as polyvinylpyrrolidone vinylacetate with neutralized crotonic acid/vinylacetate/vinylpropionate, Luviskol® with Luviset® CAP, both manufactured by BASF, see WO 94/12147 and Luviskol® with Amphomer, an amphoteric resin of octylacrylamide/acrylates/butylaminoethyl methacrylate copolymer made by National Starch, see DE 4,034, 315 A1.

The polyvinylpyrrolidone/vinyl acetate hereafter referred to as "PVP/VA" copolymers have been used in several dual resin compositions. By themselves, they have been successfully marketed as a single resin system for years for their overall grouping of properties, but the major property of a hair fixative, namely its "hold" property can be improved. Other synthetic polymers have better "hold" properties but lack other attributes which would bring about a high quality hair fixative formulation.

It has now been discovered that a high molecular weight copolymer of PVP/VA can be successfully combined with a copolymer comprising t-butyl acrylate, ethylacrylate, methacrylic acid, obtained as Luvimer® 100P from BASF, and obtain a highly desirable and surprising mix of properties, featuring high hold properties which neither polymer alone possesses and which a mixture of the Luvimer® 100P with the usual PVP/VA molecular weight copolymer does not appear to possess.

SUMMARY OF THE INVENTION

In accordance with the invention there is a sprayable hair fixing composition comprising
a. from about 0.5 to about 10 wt. % of a high molecular weight copolymer of PVP/VA, the weight average molecular weight of said copolymer being at least about 200,000,
b. from about 0.5 to about 8 wt. % of at least about 80 wt. % neutralized copolymer of tertiary butylacrylate, ethyl acrylate and methacrylic acid, and
c. a solvent system compatible with the combination of copolymer a and copolymer b the wt. % of a to b, in the range about 1 to about 4 and about 4 to about 1.

It should be noted that there can be chemical reactions between and among the components listed above and any other component which may be present in the composition. Therefore, it is intended to include such reaction product within the claimed composition as well.

DETAILED DESCRIPTION OF THE INVENTION

The high molecular weight copolymer comprising PVP/VA is obtained from BASF as Luviskol® 37HM. Generally, the weight average molecular weight as measured by light scattering is above about 200,000 preferably above about 400,000. The maximum molecular weight is at least partially dependent upon the resin combination. However, the resin combination should have the property of ready dispersibility from the container as well as compatibility with the other copolymer and system components. Generally the weight average molecular weight should not be more than about 1,000,000, preferably not more than about 800,000. A range of about 550,000 to about 700,000 is preferred. The amount of each monomer in the polymer is preferably from about 20 to about 50 wt. % vinylpyrrolidine (VP) and about 80 to about 50 wt. % vinylacetate (VA), more preferably about 25 to 40 wt. % VP and about 75 to about 60 wt. % VA. Especially preferred is the ratio of about 30 wt. % VP and about 70 wt. % VA available commercially from BASF as Luviskol® VA 37HM. The PVP/VA copolymer is preferably in the hair composition at quantities of from about 1 to about 6 wt. %.

The second copolymer comprises t-butylacrylate, ethyl acrylate, and methacrylic acid. The polymer is generally at least about 80% neutralized, preferably at least about 90% neutralized, and can be 100% neutralized. Any basic neutralizing agent compatible with the composition can be employed even inorganic materials such as sodium or potassium hydroxide. Generally organic amines or alkanolamines are readily used for neutralization.

Examples of such amines include:
triethanolamine
2-amino-2-methyl-1,3-propanediol
2-amino-2-ethyl-1,3-propanediol
2-amino-2-methyl-1-propanol
2-amino-2-methyl-2-pentanol
1-amino-2-methyl-2-propanol
2-amino-1-butanol
3-amino-2-pentanol
2-amino-1-phenyl-1-butanol
2-dimethylamino-2-methyl-1-propanol
2-dimethylamino-2-methyl-1,3-propandiol
tris-(hydroxymethyl)-aminomethane
tris-(hydroxymethyl)-dimethylaminomethane
$N^1$-(2-hydroxyethyl)-2-methyl-1,2-propandiamine
Neutralization with 2-amino-2-methyl-1-propanol or 2-amino-2-methyl-1-3-propandiol or triethanolamine is preferred.

The quantity of partially or completely neutralized acrylate/acrylic acid polymer present in the composition is preferably about 1 to about 6 wt. %. Preferably polymer a and polymer b are present in the composition in a weight ratio of about 1:3 to about 3:1.

The vehicles which carry the polymers are generally alcoholic or hydroalcoholic. The alcohol contained in the hair fixing composition is one of the common lower alcohols, such as isopropanol and ethanol, typically used in similar types of hair fixing compositions. The alcohol can be used in amounts between about 10% to about 90% by weight of the composition, preferably about 15% to about 85%.

The hair fixing composition can contain a total water content of 0 up to about 20% by weight, a water content of about 0.5 to about 15% by weight being preferred.

The hair fixing composition can have pH values of between 4.5–9.5.

The composition can also contain other typical cosmetic ingredients such as perfume, oils, extracts, vitamins and their derivatives/precursors, plasticizing agents, hydrophobing substances such as silicone derivatives, solubilizers for oils, and preservatives up to 1% each by weight if found to be advantageous to the composition.

The hair fixing composition can be filled into pressurizable containers, preferably with a propellent added or utilized as a non-propellent hair styling product.

When the composition is utilized as an aerosol hair fixing product, it contains an additional about 5 to about 75% by weight of the total composition, preferably about 25% to about 70% by weight of a propellent and is filled into an appropriate pressurizable container.

Suitable propellents for the hair fixing composition include the lower alkanes such as n-butane, iso-butane, propane and mixtures thereof with fluorocarbon 152a and dimethylether as well as compressed gases such as $N_2$, $N_2O$, $CO_2$ and mixtures thereof with the above-mentioned propellents.

When the composition is present as a non-aerosol hairspray or concentrated hairspray, the composition can be sprayed by utilizing a satisfactory mechanically operated spray pump device.

A mechanically operated spray pump device allows a liquid to be sprayed without use of propellents as listed above. An example, but not limited to that is a spray pump or an elastic container equipped with an attached spraying valve in which the hair fixing composition is filled under high pressure expanding the container and in which the composition is actuated upon opening the spraying valve can be used as a suitable spraying device/package.

The hair fixing composition is excellently compatible with halogen-free hydrocarbons and results in outstanding hair fixing properties.

The following examples serve to explain the subject matter of the composition more fully and are not intended to unduly narrow the invention. In the text below VP is the abbreviation for vinylpyrrolidone and VA is the abbreviation for vinyl acetate.

EXAMPLES

Example 1

| Aerosol hair spray Component | wt. % |
|---|---|
| Denatured Ethanol | 36.665 |
| Deionized Water | 0.125 |
| Acrylates Copolymer (Luvimer ® 100P copolymer by BASF) | 3.00 |
| Aminomethyl propanol | 0.71 |
| Fragrance | 0.30 |
| Phenyl Trimethicone | 0.20 |
| PVP/VA Copolymer (Luviskol ® VA 37HM copolymer by BASF)* | 3.00 |
| Dimethylether | 33.60 |
| N-butane | 22.40 |
| | 100.00 |

*30 wt. % VP, 70 wt. % VA, weight average molecular weight of 600,000–650,000

Example 2

| Non-aerosol hair spray Component | wt. % |
|---|---|
| Denatured Ethanol | 78.81 |
| Vinylpyrrolidone-vinyl acetetate copolymer 50% solution in ethanol (Luviskol ® VA 37HM copolymer by BASF)* | 4.00 |
| Acrylates Copolymer | 4.00 |

| Non-aerosol hair spray Component | wt. % |
|---|---|
| (Luvimer ® 100P copolymer by BASF) | 0.94 |
| 2-amino-2-methyl-1-propanol | |
| Deionized Water | 12.00 |
| Fragrance | 0.250 |
| | 100.00 |

*30 wt. % VP, 70 wt. % VA, weight average molecular weight of 600,000 to 650,000.

Comparative Performance Evaluation

The aerosol hairspray Example 1 of the invention was compared to hairspray A, hairspray B and hairspray C. Hairsprays A–C are also propellent-type hairspray but are different from the invention in that that hairsprays A–C contain the acrylates copolymer of the invention in combination with commercially available vinyl PVP/VA copolymers of various monomer ratios having weight average molecular weights as presented in BASF brochures. This is substantially lower than the 200,000 minimum weight average molecular called for in this invention. The hairsprays were evaluated with regard to the physical performance properties of the hairspray such as high humidity curl retention and hair properties evaluated via mannequin head salon evaluation. Further, the hydrocarbon tolerance/compatibility of the stated formulations were evaluated.

In addition, comparative tests were conducted on hairsprays D–E which are propellent-type compositions different from the invention containing either of the following; 1) a single resin system in the same amount as hairsprays A–C of a high molecular weight vinyl-pyrrolidone-vinyl acetate copolymer 2) a single resin system in the same amount as hairsprays A–C comprising a t-butyl acrylate, ethyl acrylate, methacrylic acid copolymer of the invention. Both hairsprays D and E were also compared to Example 1 of the invention.

| Aerosol Hairspray Component | wt. % |
|---|---|
| Hairspray A | |
| Denatured Ethanol | 36.665 |
| Deionized Water | 0.125 |
| Acrylates Copolymer (Luvimer ® 100P by BASF) | 3.000 |
| Aminomethyl propanol | 0.71 |
| Fragrance | 0.300 |
| Phenyl Trimethicone | 0.200 |
| *PVP/VA copolymer (Luviskol ® VA 371) | 3.000 |
| Dimethylether | 33.600 |
| N-butane | 22.400 |
| | 100.00 |
| *30 wt, % VP, 70 wt. % VA | |
| Hairspray B | |
| Denatured Ethanol | 36.665 |
| Deionized Water | 0.125 |
| Acrylates Copolymer (Luvimer ® 100P by BASF) | 3.000 |
| Aminomethyl propanol | 0.71 |
| Fragrance | 0.300 |
| Phenyl Trimethicone | 0.200 |
| *PVP/VA copolymer (Luviskol ® VA 55E by BASF) | 3.000 |
| Dimethylether | 33.60 |
| N-butane | 22.400 |
| | 100.00 |

-continued

| Aerosol Hairspray Component | wt. % |
|---|---|
| *50 wt. % PVP, 50 wt. % VA | |
| Hairspray C | |
| Denatured Ethanol | 36.665 |
| Deionized Water | 0.125 |
| Acrylates Copolymer (Luvimer ® 100P by BASF) | 3.000 |
| Aminomethyl propanol | 0.71 |
| Fragrance | 0.300 |
| Phenyl Trimethicone | 0.200 |
| *PVP/VA copolymer (Luviskol ® VA 73E) | 3.000 |
| Dimethylether | 33.600 |
| N-butane | 22.400 |
| | 100.00 |
| *70 wt. % PVP, 30 wt. % VA | |
| Hairspray D | |
| Denatured Ethanol | 37.815 |
| Deionized Water | 0.125 |
| Acrylates Copolymer (Luvimer ® 100P copolymer by BASF) | 4.500 |
| 2-amino-2-methyl-1-propanol | 1.06 |
| Fragrance | 0.300 |
| Phenyl Trimethicone | 0.200 |
| Dimethylether | 33.600 |
| N-butane | 22.400 |
| | 100.00 |
| Hairspray E | |
| Denatured Ethanol | 34.375 |
| Deionized Water | 0.125 |
| Vinylpyrrolidone-vinyl acetate copolymer 50% solution in ethanol (Luviskol ® VA 37HM copolymer by BASF)* | 9.00 |
| Fragrance | 0.300 |
| Phenyl Trimethicone | 0.200 |
| Dimethylether | 33.600 |
| N-butane | 22.400 |
| | 100.00 |

*30% VP, 70% VA, weight average molecular weight of 600,000–650,000

In a standard high humidity curl retention test, the hairspray preparation according to Example 1 was compared to hair sprays A–E with regard to % curl retention upon completion of a 90-minute evaluation period. Specifically, 3 gram 8" long virgin brown European hair tresses freshly shampooed with 10% sodium laureth (2EO) sulfate solution and treated with a 3-second hair spray application are rolled onto a ⅝" diameter roller and fastened. The rolled tresses are allowed to dry in a closed cabinet with a hair dryer (at low heat setting) for 30 minutes to simulate salon drying conditions.

The tresses are unrolled on a curl retention board which contains measurement lines where initial curl length readings are taken. The curl retention boards are subsequently placed in an 85% humidity chamber maintained at a temperature of about 21.6 C. for a period of 90 minutes. Typically, eight tresses are evaluated for each treatment. Readings are taken at 15 minute intervals. Results are evaluated statistically. The results stated in Table 1 represent the average evaluation for each treatment.

TABLE 1

Curl Retention Evaluation

| | % curl retention after 90 minutes | Statistical Significance |
|---|---|---|
| Example 1 | 63.33 | |
| Hairspray A | 49.92 | * |
| Hairspray B | 55.77 | |
| Hairspray C | 60.35 | |
| Hairspray D | 69.04 | |
| Hairspray E | 51.23 | * |

Note: All significant differences are larger than 95% confidence level

As can be seen in Table 1, a statistically significant difference in humidity difference (hold) between dual resin (Example 1) and hairsprays A and E is achieved. Hairspray A is the same as Example 1 except that standard molecular weight PVP/VA is used in combination with the same resin as used in Example 1. Hairspray E uses the higher molecular wt. PVP/VA. This is strong evidence that the most important property of a hairspray retention (hold) is achieved only with the invention combination as opposed to other combinations.

A subsequent salon half-head test utilizing mannequin heads is conducted using a paired comparison randomized block design. One trained evaluator evaluates the sensory attributes for each test product. Two products are tested on each mannequin head which is previously cleaned with a standard cleaning shampoo composition. The product presentation order is randomized and evaluations are balanced to ensure equal usage on both sides of the head. The hairspray product is actuated at a distance of 7 inches from the ear forward for a period of 3 seconds in an up and down motion with a standard aerosol valve that delivers an average output of 0.8 g/second. This action allows even coverage of the respective side of the mannequin head which comprises sections of both straight and curled hair. The trained evaluator assesses the following properties; dry-time, shine, beading, tackiness, hair hold, stiffness, curl hold, brushing ease, crust-the degree to which the hair's surface has a film layer of brittle substance which may break into flake-like particles when evaluated-and flakes. A rating system for each attribute (other than drying time) utilizing a scale of 1=not at all evident, to 7=extreme is employed.

Further, the mannequin heads are also evaluated after 45-minute time period in a humidity chamber stored at about 21.6° C. and about 85% relative humidity to evaluate the properties under high humidity conditions. Data is evaluated statistically and reported. The most important attributes considered are the properties of hair hold and brushing ease after application.

Tables 2–3 display the findings for attributes as determined by the trained evaluator in the evaluation of Example 1 vs. Hairsprays B–E. An asterisk in the last column of the table denotes significant differences at the 95% confidence level, or higher, between Example 1 and Hairsprays B–E.

TABLE 2

Mannequin Head Salon Evaluation
Test I.

| Attribute | Example 1 | Hairspray B | Hairspray C | Statistical Significance |
|---|---|---|---|---|
| Pre Humidity Chamber Drying Time (seconds) | 229.00 | 270.33 | 273.67 | * |
| Shine | 4.90 | 5.83 | 4.77 | * |
| Beading | 3.13 | 1.00 | 4.67 | * |
| Stiffness | 4.80 | 5.33 | 5.87 | |
| Tackiness | 2.17 | 3.10 | 2.63 | |
| Hair Hold | 4.67 | 5.20 | 4.93 | |
| Crust | 5.37 | 5.17 | 5.77 | |
| Post Humidity Chamber | | | | |
| Shine | 4.93 | 5.93 | 4.73 | * |
| Crust | 4.57 | 4.57 | 5.77 | |
| Hair Hold | 4.57 | 5.17 | 5.17 | |
| Stiffness | 4.30 | 5.03 | 5.77 | * |
| Tackiness | 2.60 | 3.73 | 3.07 | |
| Brushing Ease | 3.93 | 2.60 | 2.87 | * |
| Flakes | 3.47 | 3.67 | 4.67 | |

Pre-humidity

Example 1 significantly faster dry-time vs. Hairsprays B/C

Hairspray B significantly higher shine vs. Example 1 and Hairspray C

Hairspray B significantly less beading vs. Example 1 and Hairspray C

Post Humidity

Hairspray C significantly higher stiffness vs. Example 1 and Hairspray B

Example 1 significantly easier brushing vs. Hairsprays B/C

Note: All significant differences are larger than 95% confidence level

As can be seen in the above table, Example 1 of the invention provides good hair hold (no significant difference) vs. Hairsprays B and C while providing the significantly improved brushing ease vs. Hairsprays B and C.

TABLE 3

Test II.

| Attribute | Example 1 | Luvimer ® Hairspray D | HM Hairspray E | Statistical Significance |
|---|---|---|---|---|
| Pre Humidity Chamber Drying Time (seconds) | 193.00 | 232.00 | 209.00 | * |
| Shine | 5.50 | 5.70 | 2.80 | * |
| Beading | 2.40 | 3.70 | 5.00 | * |
| Stiffness | 5.10 | 5.80 | 4.70 | * |
| Tackiness | 2.20 | 2.60 | 3.10 | * |
| Hair Hold | 5.40 | 5.70 | 4.60 | * |
| Crust | 5.90 | 6.40 | 4.30 | * |
| Post Humidity Chamber | | | | |
| Shine | 5.50 | 6.00 | 5.40 | * |
| Crust | 5.70 | 5.70 | 3.70 | * |
| Hair Hold | 4.80 | 5.50 | 4.40 | * |
| Stiffness | 4.70 | 5.40 | 3.90 | * |
| Tackiness | 2.20 | 2.60 | 2.60 | |
| Brushing Ease | 3.00 | 2.50 | 4.00 | * |
| Flakes | 3.70 | 4.60 | 4.10 | * |

Pre-Humidity

Example 1 significantly shorter dry-time than D and E

Example 1 significantly less beading than D

Example 1 significantly less stiffness than D

Example 1 significantly less tacky than E

Example 1 significantly higher hair hold than E

Example 1 significantly more crest than E

Post Humidity

Example 1 significantly more crest than E

Example 1 significantly higher curl hold than E

Example 1 significantly more stiffness than E

Example 1 significantly higher brushing ease than D

Example 1 significantly less flaking than D

Note: All significant differences are larger than 95% confidence level

As can be seen in Table 3 above, Example 1 (dual resin system) exhibited a high level of hair hold as exhibited by Hairspray D (single resin system). Conversely, hairspray D did not display an improved level of ease of brushing as displayed by the dual resin system of Example 1. Hairspray E (single resin system) did display the improved level of ease of brushing but did not deliver a high level of curl hold as exhibited by Example 1 of the invention. The rest of the properties, of secondary nature, show varying performance as aforementioned. For this reason, the combination of an acrylates copolymer with a high molecular weight vinyl pyrrolidone-vinyl acetate copolymer is required to deliver the appropriate combination of hold and brushing ease in a hair styling product.

Further, a standard hydrocarbon compatibility evaluation is conducted to assess the compatibility of the aerosol hair fixing compositions of the invention as described in Example 1. The testing procedure is based on International Specialty Products Company supplier methodology for evaluating propellent compatibility. By observing the cloud point of an aerosol formulation, a measure of compatability of the system is determined. An appropriate quantity of hair spray concentrate is placed into a Fisher-Porter Pressure tube which contains a thermometer. An "O"-ring is placed snugly under the curl of an aerosol seal valve and tightened appropriately to the Fisher-Porter Tube. An appropriate quantity of propellent is filled into the tube to maintain the required concentrate:propellent testing ratio. A dry ice/solvent bath is prepared in which the temperature is maintained to below minus 30 F. The Fisher-Porter Tube is placed into the dry ice bath and swirled to cool the tube contents as evenly as possible.

Periodically the tube is taken out of the dry ice bath and the temperature and clarity of solution is noted. When the test solution becomes completely cloudy or hazed the temperature is noted. Typically, a hairspray that remains clear to −20 F. is considered to display excellent propellent compatibility.

Table 4 displays hydrocarbon compatibility (cloud points) of Example 1 vs. Hair Spray A–E.

TABLE 4

Hydrocarbon Compatibility

| | Cloud point Temperature (degrees Fahrenheit) |
|---|---|
| Example 1 | clear at −20 F. |
| Hair Spray A | clear at −20 F. |

TABLE 4-continued

| Hydrocarbon Compatibility | |
|---|---|
| | Cloud point Temperature (degrees Fahrenheit) |
| Hair Spray B | clear at −20 F. |
| Hair Spray C | clear at −20 F. |
| Hair Spray D | clear at −20 F. |
| Hair Spray E | clear at −20 F. |

As can be seen in Table 4 above, Example 1 of the invention composition displays excellent compatibility (low cloud point) and does not show a decrease when D and E are combined to form Example 1. For this reason it is expected that the dual resin system would not precipitate or result in cloggage/poor spray application aesthetics due to propellent incompatibilities.

What is claimed is:

1. A sprayable hair fixing composition having the following components or reaction products comprising
   a) from about 0.5 to about 10 wt. % of a high molecular weight copolymer of polyvinylpyrrolidine and vinylacetate, the weight average molecular weight of said polymer being at least about 200,000,
   b) from about 0.5 to about 8 wt. % of at least about 80 wt. % neutralized copolymer of tertiary butylacrylate, ethyl acrylate and methacrylic acid, and
   c) a solvent system compatible with the combination of copolymer a and copolymer b, the wt. % of a and b in the range of about 1:4 to about 4:1.

2. The composition in accordance with claim 1 wherein copolymer a has a weight average molecular weight of at least about 400,000.

3. The composition in accordance with claim 1 wherein the weight average molecular weight of copolymer a is not above about 800,000.

4. The composition in accordance with claim 1 wherein copolymer a has from about 20 to about 50 wt. % vinylpyrrolidine and about 80 to about 50 wt. % vinyl acetate.

5. The composition in accordance with claim 4 wherein the vinylpyrrolidine is from about 25 to about 40 wt. % and the vinyl acetate is from about 75 to about 60 wt. %.

6. The composition in accordance with claim 1 wherein copolymer a is present in the composition in quantities of about 1 to about 6 wt. %.

7. The composition in accordance with claim 1 wherein copolymer b is at least about 90 wt. % neutralized.

8. The composition in accordance with claim 1 wherein copolymer b is present in the composition in quantities of from about 1 to about 6 wt. %.

9. The composition in accordance with claim 1 wherein alcohol or a combination of alcohol and water is present.

10. The composition in accordance with claim 9 wherein alcohol is about 10 to about 90 wt. %.

11. The composition in accordance with claim 10 wherein water is zero to about 20 wt. % of the composition.

12. The composition in accordance with claim 1 wherein the pH of the composition is between about 4.5 and about 9.5.

13. The composition in accordance with claim 1 which can be an aerosol and has a propellent therein.

14. The composition in accordance with claim 13 wherein the propellant is about 5 to about 75 wt. % of the total composition.

15. A product which comprises the composition prepared by contacting in any order
   a) from about 0.5 to about 10 wt. % of a high molecular weight copolymer of polyvinylpyrrolidine and vinylacetate, the weight average molecular weight of said polymer being at least about 200,000,
   b) from about 0.5 to about 8 wt. % of at least about 80 wt. % neutralized copolymer of tertiary butylacrylate, ethyl acrylate and methacrylic acid, and
   c) a solvent system compatible with the combination of copolymer a and copolymer b, the wt. % of a and b in the range of about 1:4 to about 4:1.

* * * * *